United States Patent
Zhao

(10) Patent No.: US 12,009,072 B2
(45) Date of Patent: Jun. 11, 2024

(54) METHOD OF DISPLAYING MEDICAL INFORMATION AND HEALTH RECORD APPARATUS

(71) Applicant: BOE TECHNOLOGY GROUP CO., LTD., Beijing (CN)

(72) Inventor: Lei Zhao, Beijing (CN)

(73) Assignee: BOE TECHNOLOGY GROUP CO., LTD., Beijing (CN)

(*) Notice: Subject to any disclaimer, the term of this patent is extended or adjusted under 35 U.S.C. 154(b) by 455 days.

(21) Appl. No.: 17/298,511

(22) PCT Filed: Nov. 24, 2020

(86) PCT No.: PCT/CN2020/130997
§ 371 (c)(1),
(2) Date: May 28, 2021

(87) PCT Pub. No.: WO2021/104223
PCT Pub. Date: Jun. 3, 2021

(65) Prior Publication Data
US 2022/0148692 A1 May 12, 2022

(30) Foreign Application Priority Data
Nov. 25, 2019 (CN) .......................... 201911169003.7

(51) Int. Cl.
*G16H 10/60* (2018.01)
*G16H 15/00* (2018.01)

(52) U.S. Cl.
CPC ............. *G16H 10/60* (2018.01); *G16H 15/00* (2018.01)

(58) Field of Classification Search
CPC ..... G06F 3/0488; G06F 16/248; G16H 10/60; G16H 15/00; G05B 19/418; G06Q 10/00
See application file for complete search history.

(56) References Cited

U.S. PATENT DOCUMENTS 10,283,088 B2 * 5/2019 Ban ........................ A61B 6/03
11,152,104 B2 * 10/2021 Konishi .................. G06F 18/24
(Continued)

FOREIGN PATENT DOCUMENTS

| CN | 105473071 A | 4/2016 |
|---|---|---|
| CN | 108628506 A | 10/2018 |
| CN | 108961125 A | 12/2018 |

OTHER PUBLICATIONS

Extended European Search Report for European Patent Application No. 20894530.3 issued by the European Patent Office dated Dec. 7, 2022.

*Primary Examiner* — Tadesse Hailu
(74) *Attorney, Agent, or Firm* — IP & T GROUP LLP

(57) ABSTRACT

A method of displaying medical information, includes: displaying a first interface; determining a target patient in response to at least a first operation of a user on the first interface; displaying a second interface in a currently set display mode; and determining a target index item in response to a second operation of the user on the second interface, and displaying medical information of the target patient matched with the target index item. The second interface presents at least index item(s) of medical information of the target patient. The target index item is one of the index item(s). The currently set display mode is one of at least two display modes including a first display mode and a second display mode, and the index items on the second interface corresponding to different display modes are different.

16 Claims, 11 Drawing Sheets

(56) References Cited

U.S. PATENT DOCUMENTS

| | | | |
|---|---|---|---|
| 11,551,789 B2* | 1/2023 | Ayers | G06F 16/248 |
| 2006/0293920 A1 | 12/2006 | Stroup et al. | |
| 2008/0065420 A1* | 3/2008 | Tirinato | G16H 10/60 |
| | | | 705/3 |
| 2009/0204440 A1* | 8/2009 | Stroup | G16H 10/40 |
| | | | 707/999.107 |
| 2014/0350961 A1 | 11/2014 | Csurka et al. | |
| 2014/0368545 A1 | 12/2014 | Ban et al. | |
| 2015/0278484 A1* | 10/2015 | Tirinato | G16H 10/40 |
| | | | 705/3 |
| 2015/0339447 A1 | 11/2015 | Kitagawa et al. | |
| 2018/0350019 A1 | 12/2018 | McLaren et al. | |
| 2019/0236499 A1* | 8/2019 | Reyes | G16H 40/20 |

* cited by examiner

METHOD OF DISPLAYING MEDICAL INFORMATION AND HEALTH RECORD APPARATUS

CROSS-REFERENCE TO RELATED APPLICATIONS

This application is a national phase entry under 35 USC 371 of International Patent Application No. PCT/CN2020/130997, filed on Nov. 24, 2020, which claims priority to Chinese Patent Application No. 201911169003.7, filed on Nov. 25, 2019, which are incorporated herein by reference in their entirety.

TECHNICAL FIELD

The present disclosure relates to the field of electronic devices, in particular, to a method of displaying medical information and a health record apparatus.

BACKGROUND

Currently, health records of patients have gradually become digitized. However, data in the health records generally cannot be shared among different medical institutions, and the data is usually presented in a monotonous way.

Thus, medical personnel cannot learn about the health condition of a patient in a comprehensive and multifaceted manner. As a result, it is not convenient for patients to get treatment, and the diagnoses of the medical personnel may not be efficient and accurate enough.

SUMMARY

In an aspect, a method of displaying medical information is provided. The method includes: displaying a first interface; determining a target patient in response to at least a first operation of a user on the first interface; displaying a second interface in a currently set display mode, the second interface presenting at least index item(s) of medical information of the target patient, the currently set display mode being one of at least two display modes including a first display mode and a second display mode, and the index item(s) on the second interface corresponding to different display modes being different; and determining a target index item, the target index item being one of the index item(s), and displaying medical information of the target patient matched with the target index item in response to a second operation of the user on the second interface.

In some embodiments, the method further includes: setting the display mode of the second interface to the first display mode in response to an instruction to switch to the first display mode, the index item(s) on the second interface displayed in the first display mode including first index item(s); and setting the display mode of the second interface to the second display mode in response to an instruction to switch to the second display mode, the index item(s) on the second interface displayed in the second display mode including second index item(s).

In some embodiments, the first index item(s) include at least one of personal self-test information, health examination, outpatient summary, maternal and child health, prophylactic vaccination, public health event report, special disease health management, hospitalization summary, consultation information, referral or transfer information.

In some embodiments, the second index item(s) include at least one medical event.

In some embodiments, the currently set display mode is the first display mode. Determining the target index item, and displaying the medical information of the target patient matched with the target index item in response to the second operation, includes: determining the target index item in response to the second operation; displaying a third interface according to the determined target index item, the third interface including a first list area and a first detail area, and the first list area presenting at least one medical event of the target patient matched with the target index item; and determining a target medical event, the target medical event being one of the at least one medical event, and presenting the medical information matched with the target medical event in the first detail area in response to a third operation of the user on the third interface.

In some embodiments, the medical information includes at least one item name and medical data corresponding to each item name. The at least one medical event includes at least two medical events. The method further includes: determining a target item name, the target item name being one of the at least one item name, and displaying a fourth interface, the fourth interface presenting medical data of the target patient matched with the target item name in the at least two medical events, in response to a fourth operation of the user on the third interface.

In some embodiments, the currently set display mode is the second display mode. Determining the target index item, and displaying the medical information of the target patient matched with the target index item in response to the second operation, includes: determining the target index item in response to the second operation; and displaying a fifth interface according to the determined target index item, the fifth interface presenting the medical information of the target patient matched with the target index item.

In some embodiments, the currently set display mode is the second display mode. The index item(s) further include a first index item corresponding to each second index item. Determining the target index item, and displaying the medical information of the target patient matched with the target index item in response to the second operation, includes: determining the target index item, the target index item being one of the second index item(s), and determining a first index item corresponding to the target index item in response to the second operation; displaying a fifth interface according to the determined first index item corresponding to the target index item, the fifth interface including a second detail area and a second list area, and the second list area presenting at least one medical event of the target patient matched with the first index item corresponding to the target index item; determining a target medical event in response to a fifth operation of the user on the fifth interface, the target medical event being one of the at least one medical event; and presenting the medical information matched with the target medical event in the second detail area in response to the fifth operation.

In some embodiments, the medical information includes at least one item name and medical data corresponding to each item name. The at least one medical event includes at least two medical events. The display further includes: determining a target item name, the target item name being one of the at least one item name, and displaying a fourth interface, the fourth interface presenting medical data of the target patient matched with the target item name in the at least two medical events, in response to a sixth operation of the user on the fifth interface.

In some embodiments, the at least two display modes further include a third display mode. The method further includes: setting the display mode of the second interface to the third display mode in response to an instruction to switch to the third display mode, the index item(s) on the second interface displayed in the third display mode including third index item(s).

In some embodiments, the third index item(s) include at least one of diagnosis, prescription, examination, test, electronic medical record, or charge.

In some embodiments, the currently set display mode is the third display mode. The second interface includes at least a third list area and a third detail area. Determining the target index item, and displaying the medical information of the target patient matched with the target index item in response to the second operation, includes: determining the target index item, the target index item being one of the third index item(s), and presenting at least one medical event matched with the target index item in the third list area in response to the second operation; and determining a target medical event, the target medical event being one of the at least one medical event, and presenting the medical information matched with the target medical event in the third detail area in response to a seventh operation of the user on the second interface.

In some embodiments, the medical information includes at least one item name and medical data corresponding to each item name. The at least one medical event includes at least two medical events. The method further includes: determining a target item name, the target item name being one of the at least one item name, and displaying a fourth interface, the fourth interface presenting medical data of the target patient matched with the target item name in the at least two medical events, in response to an eighth operation of the user on the second interface.

In some embodiments, the method further includes: obtaining medical information of a plurality of patients from servers of a plurality of medical institutions, and storing the medical information in a database. Determining the target index item, and displaying the medical information of the target patient matched with the target index item in response to the second operation, includes: determining the target index item, obtaining the medical information of the target patient matched with the target index item from the database, and displaying the medical information in response to the second operation.

In a second aspect, a health record apparatus is provided. The health record apparatus includes a display and a processor, and the processor is coupled to the display. The display is configured to display images. The processor is configured to: control the display to display a first interface; determine a target patient in response to at least a first operation of the user on the first interface; control the display to display a second interface in a currently set display mode according to the determined target patient, the second interface presenting at least index item(s) of medical information of the target patient, the currently set display mode being one of at least two display modes including a first display mode and a second display mode, and the index item(s) on the second interface corresponding to different display modes being different; determine a target index item in response to a second operation of the user on the second interface, the target index item being one of the index item(s); and control the display to display medical information of the target patient matched with the target index item according to the determined target index item.

In some embodiments, the processor is further configured to: set the display mode of the second interface to the first display mode in response to an instruction to switch to the first display mode, the index item(s) on the second interface displayed in the first display mode including first index item(s); and set the display mode of the second interface to the second display mode in response to an instruction to switch to the second display mode, the index item(s) on the second interface displayed in the second display mode including second index item(s).

In some embodiments, the at least two display modes further include a third display mode. The processor is further configured to set the display mode of the second interface to the third display mode in response to an instruction to switch to the third display mode. The index item(s) on the second interface displayed in the third display mode include third index item(s).

In some embodiments, the processor is further configured to obtain medical information of a plurality of patients from servers of a plurality of medical institutions. The health record apparatus further includes a memory coupled to the processor. The memory is configured to store the medical information of the plurality of patients obtained by the processor in a database. The processor is further configured to obtain the medical information of the target patient matched with the target index item from the database according to the determined target index item, so as to control the display to display the medical information.

In a third aspect, a computer device is provided. The computer device includes a memory and a processor. The memory has stored thereon computer program instructions that are executable on the processor. The method of displaying medical information as described above is implemented when the processor executes the computer program instructions.

In a fourth aspect, a non-transitory computer-readable storage medium is provided. The non-transitory computer-readable storage medium has stored thereon computer program instructions. When the computer program instructions run on a processor, the processor executes one or more steps in the method of displaying medical information as described above.

BRIEF DESCRIPTION OF THE DRAWINGS

In order to describe technical solutions in the present disclosure more clearly, the accompanying drawings to be used in some embodiments of the present disclosure will be introduced briefly below. Obviously, the accompanying drawings to be described below are merely accompanying drawings of some embodiments of the present disclosure, and a person of ordinary skill in the art may obtain other drawings according to these drawings. In addition, the accompanying drawings to be described below may be regarded as schematic diagrams, and are not limitations on an actual size of a product, an actual process of a method and an actual timing of a signal involved in the embodiments of the present disclosure.

FIG. 7B is a schematic diagram of another third interface, in accordance with some embodiments;

FIG. 9 is a schematic diagram of a second interface displayed in a third display mode, in accordance with some embodiments;

FIG. 10 is a schematic diagram of another second interface displayed in a third display mode, in accordance with some embodiments;

FIG. 11 is a schematic diagram of yet another second interface displayed in a third display mode, in accordance with some embodiments;

FIG. 12A is a schematic diagram of yet another second interface displayed in a third display mode, in accordance with some embodiments;

DETAILED DESCRIPTION

Figure 1:
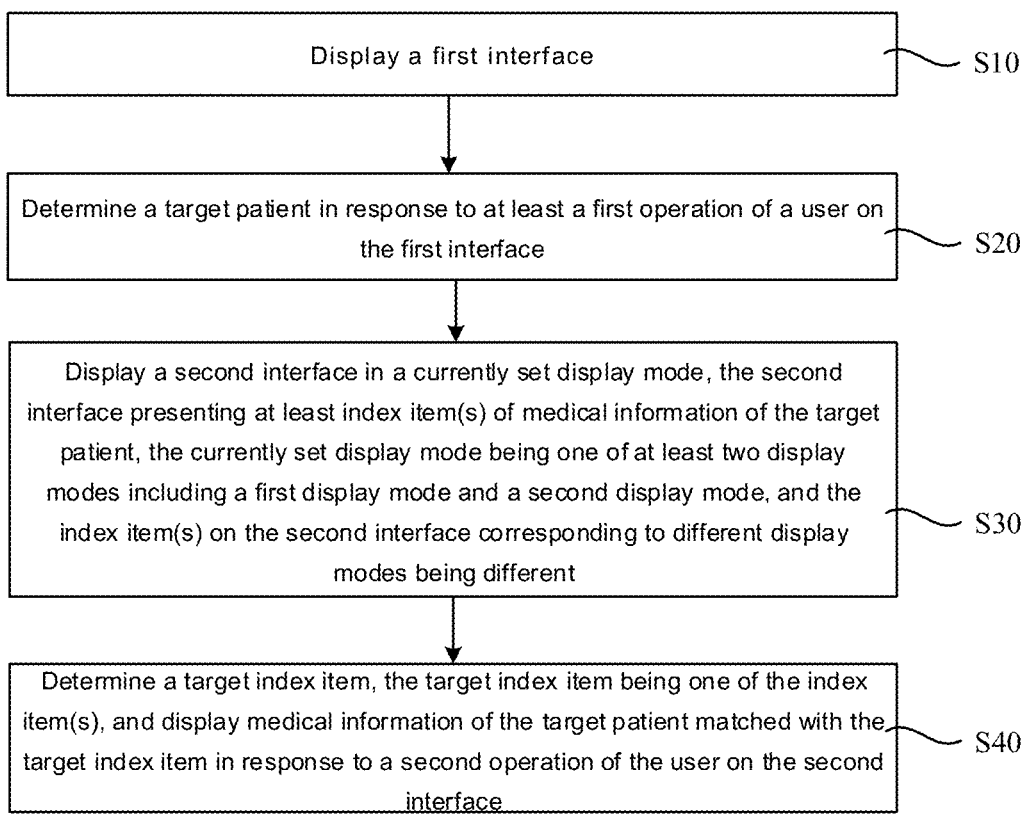
FIG. 1 is a flow diagram of a method of displaying medical information, in accordance with some embodiments.

The technical solutions in some embodiments of the present disclosure will be described clearly and completely below with reference to the accompanying drawings. Obviously, the described embodiments are merely some but not all of the embodiments of the present disclosure. All other embodiments obtained by a person of ordinary skill in the art on a basis of the embodiments of the present disclosure shall be included in the protection scope of the present disclosure.

Unless the context requires otherwise, throughout the description and the claims, the term "comprise" and other forms thereof such as the third-person singular form "comprises" and the present participle form "comprising" are construed as an open and inclusive meaning, i.e., "including, but not limited to." In the description of the specification, the terms such as "one embodiment", "some embodiments", "exemplary embodiments", "an example", "specific example" or "some examples" are intended to indicate that specific features, structures, materials or characteristics related to the embodiment(s) or example(s) are included in at least one embodiment or example of the present disclosure. Schematic representations of the above terms do not necessarily refer to the same embodiment(s) or example(s). In addition, the specific features, structures, materials, or characteristics may be included in any one or more embodiments or examples in any suitable manner.

Below, the terms "first" and "second" are used for descriptive purposes only, and are not to be construed as indicating or implying the relative importance or implicitly indicating the number of indicated technical features. Thus, a feature defined with "first" or "second" may explicitly or implicitly include one or more of the features. In the description of the embodiments of the present disclosure, "a plurality of/the plurality of" means two or more unless otherwise specified.

In the description of some embodiments, the term "coupled" and derivatives thereof may be used. For example, the term "coupled" may be used in the description of some embodiments to indicate that two or more components are in direct physical or electrical contact with each other. However, the term "coupled" may also mean that two or more components are not in direct contact with each other, but still cooperate or interact with each other. The embodiments disclosed herein are not necessarily limited to the content herein.

The use of the phrase "configured to" is meant as an open and inclusive expression, which does not exclude devices that are configured to perform additional tasks or steps.

In addition, the use of the phrase "based on" is meant to be open and inclusive, since a process, step, calculation or other action that is "based on" one or more of the stated conditions or values may, in practice, be based on additional conditions or values other than those stated.

The interfaces described in the embodiments of the present disclosure may be the same interface or different interfaces.

Some embodiments of the present disclosure provide a method of displaying medical information. A main body of implementation of the method of displaying medical information provided in the embodiments of the present disclosure is an electronic device. The electronic device is, for example, a mobile phone, a tablet computer, a handheld computer, a notebook computer, a personal computer (PC), or any other product or component having a display function, and the embodiments of the present disclosure do not specially limit the type of the electronic device.

As shown in FIG. 1, the method of displaying medical information includes S10 to S40.

In S10, the electronic device displays a first interface.

In S20, the electronic device determines a target patient in response to at least a first operation of a user on the first interface.

Figure 2:
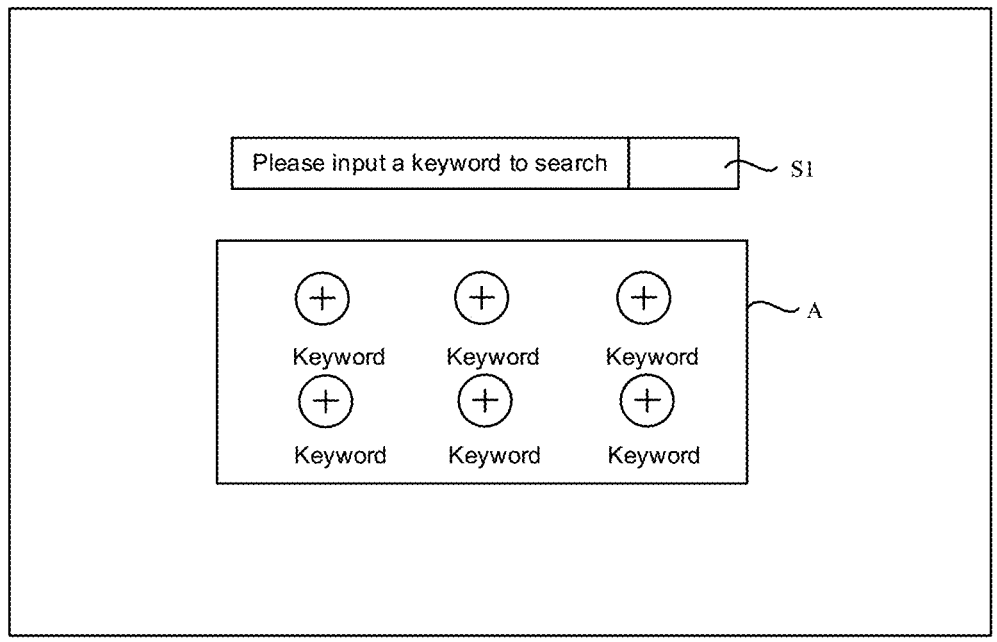
FIG. 2 is a schematic diagram of a first interface, in accordance with some embodiments.

In some examples, as shown in FIG. 2, the first interface displayed by the electronic device is a search interface, and the search interface includes a first search box S1. The description that the electronic device responds to at least the first operation of the user on the first interface in S20 means that the electronic device responds to at least the first operation of the user on the search interface. The first operation may be understood as: inputting a keyword into the first search box S1 on the search interface.

For example, the user performs a search by inputting an ID number that is uniquely associated with the target patient as the keyword into the first search box S1. In response to the first operation (i.e., inputting the ID number) of the user on the search interface, the electronic device will present a patient matched with the ID number on the first interface, the patient being the target patient.

Figure 3:
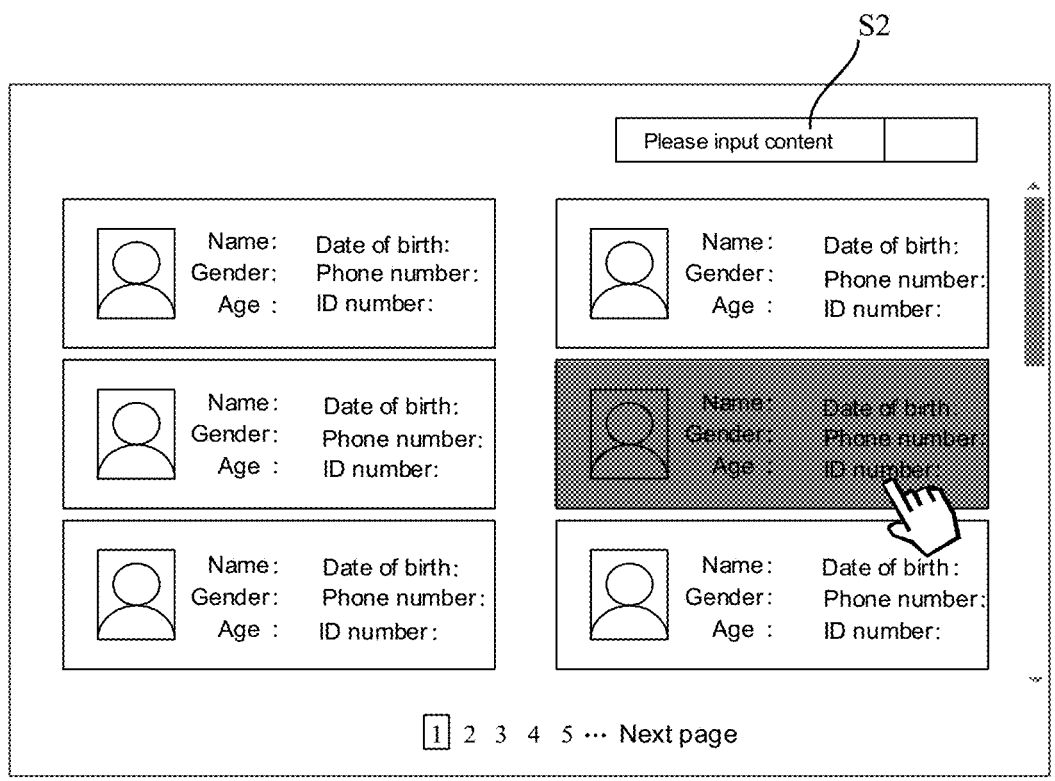
FIG. 3 is a schematic diagram of another first interface, in accordance with some embodiments.

For another example, the user performs a search by inputting a name as the keyword into the first search box S1. In response to the first operation (i.e., inputting the name) of the user on the search interface, the electronic device will display a patient list interface (as shown in FIG. 3), the patient list interface presenting at least one name identical to the name and basic information of patient(s) matched with respective name(s). Herein, the basic information includes at least one of name, photo, gender, date of birth, age, phone number, ID number, contact person, and contact person's phone number.

On this basis, the electronic device determines the target patient in response to an operation of the user clicking on one of the names.

Or, as shown in FIG. 3, the patient list interface may further include a second search box S2. In a case where the patient list interface presents a plurality of identical names and basic information of patients matched with respective names, the user may perform a search by inputting other basic information except for the name as the keyword into the second search box S2. The electronic device will determine the target patient in response to the keyword (for example, the age of the target patient "ZHANG San") input by the user on the patient list interface.

In some other examples, as shown in FIG. 2, the first interface is a search interface, and the search interface further includes a display area A.

For example, the display area A is located below the first search box. The display area is used to display search history records. The search history records refer to words that the user has searched multiple times during usage, or a plurality of words that the user has searched before this search, the plurality of words being displayed in a reverse order (e.g., from a most recently entered keyword to a sixth last keyword).

In S30, the electronic device displays a second interface in a currently set display mode. The second interface presents at least index item(s) of medical information of the target patient.

In the embodiments of the present disclosure, the medical information refers to medical-related data of the target patient, which includes time, location, medical examination, test item name and corresponding data, diagnosis result, prescription, and hospitalization information. The index item refers to a sign on the second interface that serves as a guide. Through the index item(s), it is convenient for the user to find the medical information of the target patient. In the embodiments of the present disclosure, the user refers to a doctor or other medical workers. In order to protect the privacy of the patient, the method of displaying medical information in the embodiments of the present disclosure may give different permissions to different users.

Herein, the currently set display mode is one of at least two display modes, and the index item(s) on the second interface corresponding to different display modes are different. The at least two display modes include a first display mode and a second display mode. In this way, the user may switch between different display modes according to their own preferences and usage habits during use.

It will be noted that a method of setting the display mode is not limited here. The display mode may be a default display mode in the system setting, or may be set in advance by the user.

In some examples, the second interface further presents the basic information of the target patient.

Items of the basic information of the target patient presented on the second interface may be the same as or different from the items of the basic information of the patient presented on the patient list interface, which is not limited in the embodiments of the present disclosure. For example, the items of the basic information of the patient presented on the patient list interface include profile picture, name, gender, and age, and the items of the basic information of the target patient presented on the second interface include profile picture, name, gender, age, date of birth, phone number, ID number, and address.

In S40, the electronic device determines a target index item, and displays the medical information of the target patient matched with the target index item in response to a second operation of the user on the second interface. The target index item is one of the index item(s).

Here, the second operation may be understood as a click operation.

In the method of displaying medical information provided in some embodiments of the present disclosure, the electronic device displays the first interface, then determines the target patient in response to at least the first operation of the user on the first interface, and displays the second interface in the currently set display mode according to the determined target patient. On this basis, the electronic device determines the target index item, and displays the medical information of the target patient matched with the target index item in response to the second operation of the user on the second interface. Since the currently set display mode is one of the at least two display modes, and the index item(s) on the second interface corresponding to different display modes are different, the user may select different display modes to view the medical information of the target patient according to their preferences and usage habits, so as to learn about the target patient in a comprehensive and multifaceted manner, and provide strong support for the treatment of the target patient.

In some embodiments, the method of displaying medical information further includes S50 and S60.

In S50, the electronic device sets the display mode of the second interface to the first display mode in response to an instruction to switch to the first display mode. The index item(s) on the second interface displayed in the first display mode include first index item(s).

In S60, the electronic device sets the display mode of the second interface to the second display mode in response to an instruction to switch to the second display mode. The index item(s) on the second interface displayed in the second display mode include second index item(s).

Figure 4:
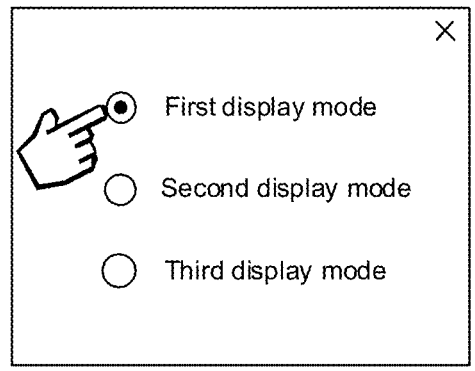
FIG. 4 is a schematic diagram of setting an interface of a display mode, in accordance with some embodiments.

In some examples, the electronic device displays a display mode setting interface in response to an instruction, given by the user on the first interface or the second interface, to set the display mode. As shown in FIG. 4, the display mode setting interface presents at least two options corresponding to different display modes such as the first display mode and the second display mode. When the user selects the "First display mode" option on the display mode setting interface, the electronic device sets the display mode of the second interface to the first display mode in response to the instruction to switch to the first display mode. When the user selects the "Second display mode" option on the display mode setting interface, the electronic device sets the display mode of the second interface to the second display mode in response to the instruction to switch to the second display mode.

In some examples, the first index item(s) include at least one category of personal self-test information, health examination, outpatient summary, maternal and child health, prophylactic vaccination, public health incident report, special disease health management, hospitalization summary, consultation information, referral or transfer information.

The category of the first index item may be classified based on the standard of the medical service industry of the People's Republic of China (WS 365-2011: Basic Dataset of Health Records for Urban and Rural Residents). For example, according to the Basic Dataset of Health Records for Urban and Rural Residents, items such as measurement item name, measurement result value, measurement date, sign (normal or abnormal), and reference range are classified as personal self-test information; items such as body temperature, pulse rate, respiratory rate, height, weight, waist circumference, and body mass index are classified as health examination; items such as name of medical institution, code of medical institution, name of department, and time of treatment are classified as outpatient summary; items such as newborn, child health, prenatal follow-up visit, and puerperal visit are classified as maternal and child health; items such as name of vaccine, vaccination date, and number of vaccine doses are classified as prophylactic vaccination; items such as infectious disease report and occupational disease report are classified as public health incident report; items such as follow-up of hypertensive patients and follow-up of diabetic patients are classified as special disease health management; items such as the name of hospitalization institution, code of hospitalization institution, name of admission department, time of admission, and reason of admission are classified as hospitalization summary; items such as reason of consultation, consultation opinion, and consultation date are classified as consultation information; items such as name of transfer-in medical institution, name of department of transfer-in institution, name of transfer-out medical institution, and reason of referral are classified as referral or transfer information.

In addition, the user may add or remove a first index item presented on the second interface as needed. The user may also sort the first index items as needed.

Figure 5:
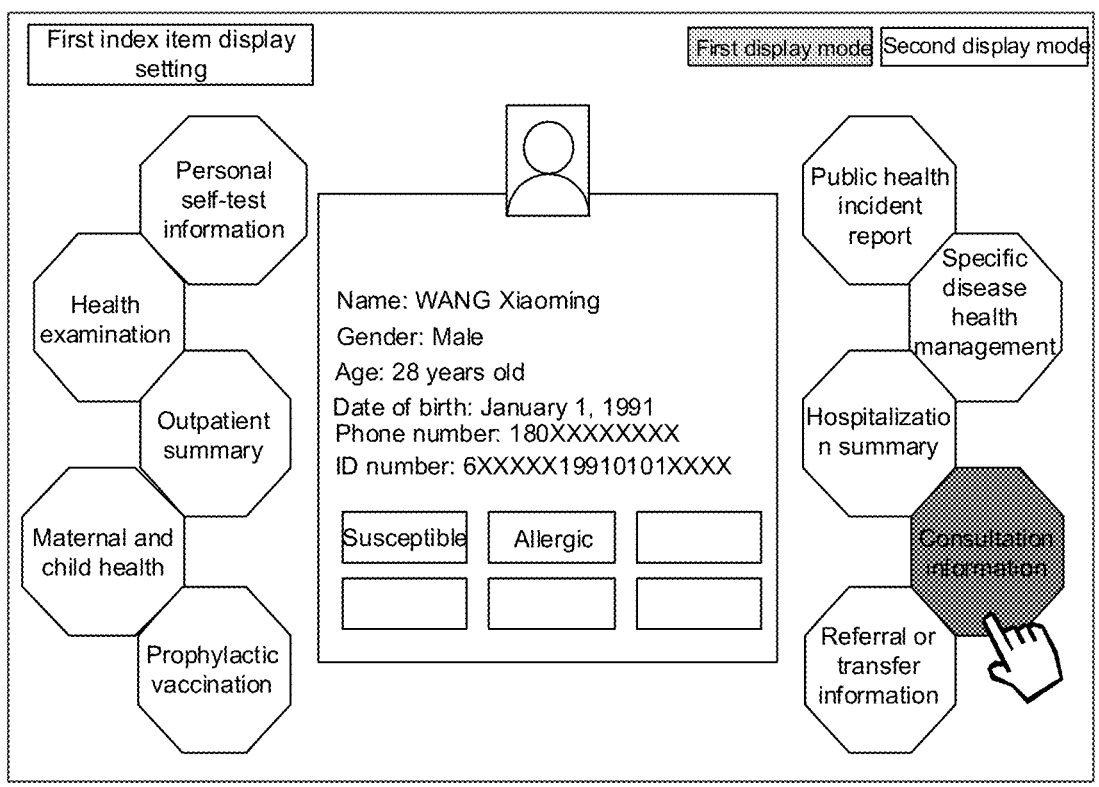
FIG. 5 is a schematic diagram of a second interface displayed in a first display mode, in accordance with some embodiments.

For example, as shown in FIG. 5, the second interface further presents a setting option of "First index item display setting". The electronic device displays a first index item display setting interface in response to an instruction (e.g., clicking the setting option) of the user to set the display manner of the first index item(s) on the second interface.

Figure 6:
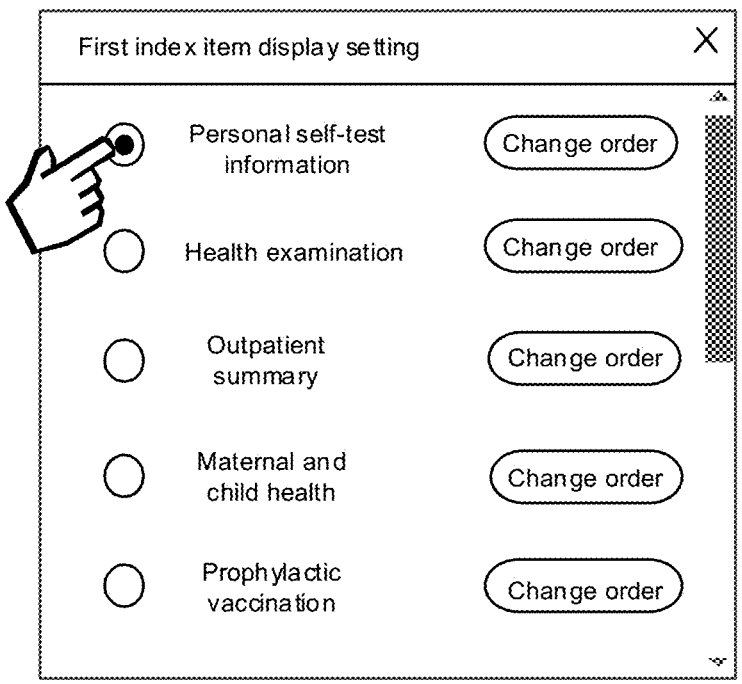
FIG. 6 is a schematic diagram of setting an interface of a first index item, in accordance with some embodiments.

As shown in FIG. 6, the first index item display setting interface presents all of the first index items and check boxes corresponding to respective first index items. The user may check the check box corresponding to any first index item to add the first index item to the second interface for presentation, or uncheck the check box corresponding to any first index item to hide the first index item from the second interface.

For example, as shown in FIG. 6, the first index item display setting interface further presents "Change order" options corresponding to respective first index items. The user may drag the "Change order" option corresponding to any first index item to move the first index item forwards or backwards according to the their own preferences. The electronic device presents the plurality of first index items arranged in different orders on the second interface in response to the drag operation of the user on the interface of setting the first index items.

In some examples, the second index item(s) include at least one medical event.

In the embodiments of the present disclosure, the medical event refers to a medical-related event of the target patient, such as consultation or hospitalization in a certain hospital on a certain day.

In some examples, as shown in FIG. 5, the second interface further includes a basic information column of the target patient. The basic information column of the target patient presents the basic information of the target patient. For example, the basic information column of the target patient presents the photo, name, gender, age, ID number, phone number, etc. of the target patient.

On this basis, the basic information column of the target patient further presents at least one label matched with the target patient. The label(s) are used to describe a special situation of the target patient, so as to remind medical personnel to pay attention to the special situation of the target patient. For example, the label says "Susceptible", "Allergic", etc., indicating that the target patient is susceptible or allergic.

In some embodiments, the currently set display mode is the first display mode, and S40 includes S411 to S413.

In S411, the electronic device determines the target index item in response to the second operation of the user on the second interface. The target index item is one of the first index item(s).

In some examples, as shown in FIG. 5, the currently set display mode is the first display mode, and a plurality of first index items presented on the second interface displayed in the first display mode include personal self-test information, health examination, outpatient summary, maternal and child health, prophylactic vaccination, public health incident report, special disease health management, hospitalization summary, consultation information, referral or transfer information. The electronic device determines that the target index item is one of personal self-test information, health examination, outpatient summary, maternal and child health, prophylactic vaccination, public health incident report, special disease health management, hospitalization summary, consultation information, referral or transfer information in response to the second operation (e.g., clicking on one of the plurality of first index items) of the user on the second interface.

For example, as shown in FIG. 5, the second operation of the user on the second interface may be clicking on consultation information. Then, the electronic device will determine that the target index item is consultation information in response to the second operation of the user on the second interface.

In S412, the electronic device displays a third interface according to the determined target index item. The third interface includes a first list area (the area indicated by B1 in FIG. 7A or 7B) and a first detail area (the area indicated by C1 in FIG. 7B). The first list area presents at least one medical event of the target patient matched with the target index item. The first detail area presents medical information of the target patient matched with one medical event.

It will be noted that the medical event(s) of the target patient matched with the target index item may not exist or may include one or more medical events. The embodiments of the present disclosure are described by taking an example in which there is at least one medical event matched with the target index item. It can be understood that in a case where no medical event of the target patient matches with the target index item, the first list area on the third interface will not present any content, and the corresponding first detail area also will not present any content either.

In some examples, in the case where a plurality of medical events of the target patient match with the target index item, the plurality of medical events are arranged in a reverse chronological order. For example, the last medical event is displayed at the top of the first list area. On this basis, the first detail area may present the medical information of the medical event arranged at the top of the first list area by default.

Figure 7A:
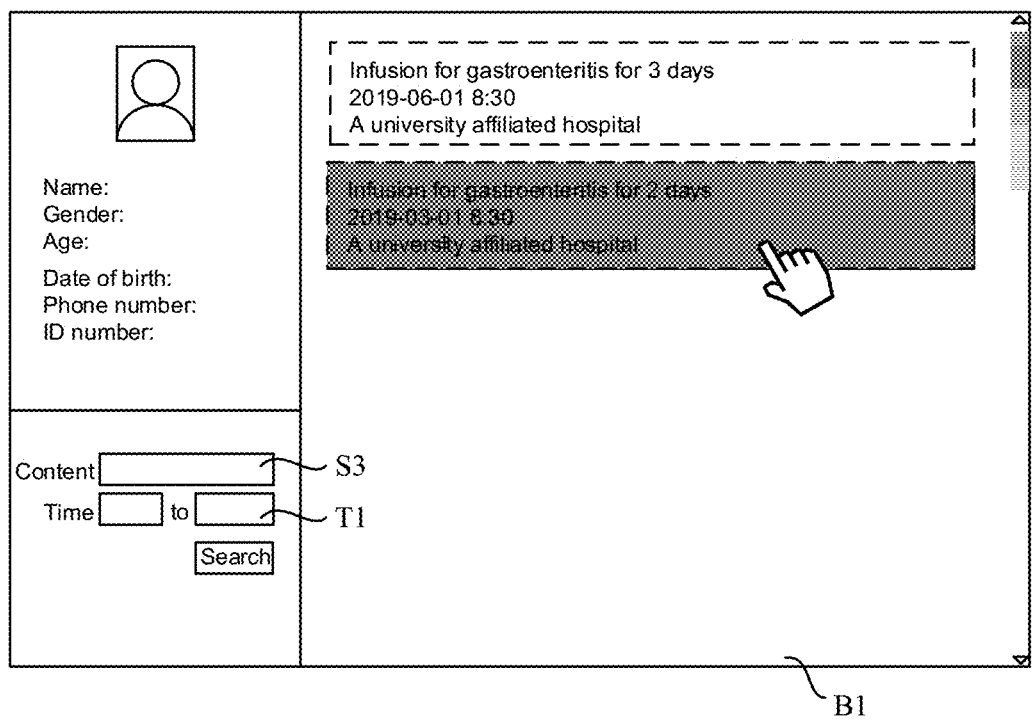
FIG. 7A is a schematic diagram of a third interface, in accordance with some embodiments.
Figure 7B:
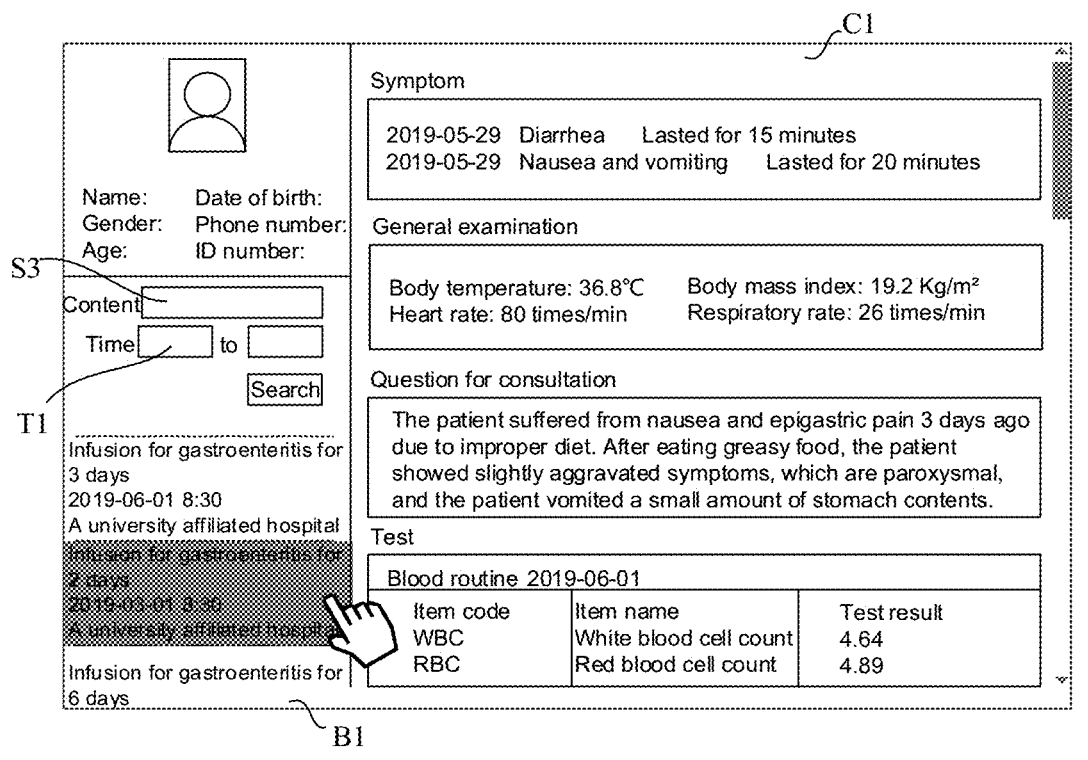

For example, if the target patient is "WANG Xiaoming", and the target index item is "Outpatient summary", then as shown in FIGS. 7A and 7B, the first list area on the third interface presents all medical events of the patient "WANG Xiaoming" matched with the first index item of "Outpatient summary". For example, one medical event is "Infusion for gastroenteritis for 3 days 2019-06-01 8:30 A university affiliated hospital", and another medical event is "Infusion for gastroenteritis for 2 days 2019-03-01 8:30 A university affiliated hospital". The medical event dated "2019-06-01 8:30" is presented at the top of the first list area, and the first detail area presents the medical information of the medical event, such as symptom, general examination, question for consultation, and test.

In S413, the electronic device determines a target medical event, and presents the medical information matched with the target medical event in the first detail area in response to a third operation of the user on the third interface. The target medical event is one of the at least one medical event.

In some examples, the first list area on the third interface presents the at least one medical event of the target patient matched with the target index item. The electronic device determines that a medical event is the target medical event in response to the third operation (e.g., clicking on one of the medical events) of the user on the third interface.

For example, as shown in FIG. 7B, the third operation of the user on the third interface may be clicking on the medical event "Infusion for gastroenteritis for 2 days 2019-03-01 8:30 A university affiliated hospital". Then, the electronic device determines that the medical event "Infusion for gastroenteritis for 2 days 2019-03-01 8:30 A university affiliated hospital" is the target medical event, and presents the medical information matched with the target medical event in the first detail area in response to the third operation of the user on the third interface.

In some examples, as shown in FIGS. 7A and 7B, the third interface further includes a third search box S3. The user may input a keyword (such as "gastroenteritis") related to the medical event presented in the first list area into the third search box S3, then the electronic device may only present the medical event(s) related to gastroenteritis in the first list area in response to the keyword "gastroenteritis" input by the user into the third search box S3.

In some examples, the third interface further includes a plurality of time options. Based on this, the user can filter the medical event(s) through the time option. For example, the plurality of time options are "YYYY-MM-DD to YYYY-MM-DD" (the option indicated by T1 in FIG. 7A or 7B; "YYYY" indicates the year, "MM" indicates the month, and "DD" indicates the date), "In the last three months", "In the last six months" and "In the last year". If the user selects the time option of "In the last six months", then the first list area on the third interface correspondingly present all medical events of the target patient matched with the target index item within six months before the time of the users current operation.

In some other examples, the third interface further presents a time selector. The user can filter the medical event(s) that occur at a certain time as needed. For example, the user may select "2019-11-03" to filter out medical event(s) that occurred on the day of Nov. 3, 2019.

In some other embodiments, the currently set display mode is the first display mode, and S40 includes S411' to S413'.

S411' and S412' are respectively the same as S411 and S412 in the above embodiments, and details will not be repeated here.

In S413', the electronic device determines a target medical event, and displays the medical information matched with the target medical event in response to a third operation input by the user on the third interface. The target medical event is one of the at least one medical event.

In some examples, S413' includes that: the electronic device determines the target medical event in response to the third operation input by the user on the third interface, and displays a detail interface according to the determined target medical event. The detail interface presents the medical information matched with the target medical event.

In some embodiments, the currently set display mode is the second display mode, and S40 includes S421 and S422.

In S421, the electronic device determines the target index item in response to the second operation of the user on the second interface. The target index item is one of the second index item(s).

In S422, the electronic device displays a fifth interface according to the determined target index item. The fifth interface presents the medical information of the target patient matched with the target index item.

Figure 8:
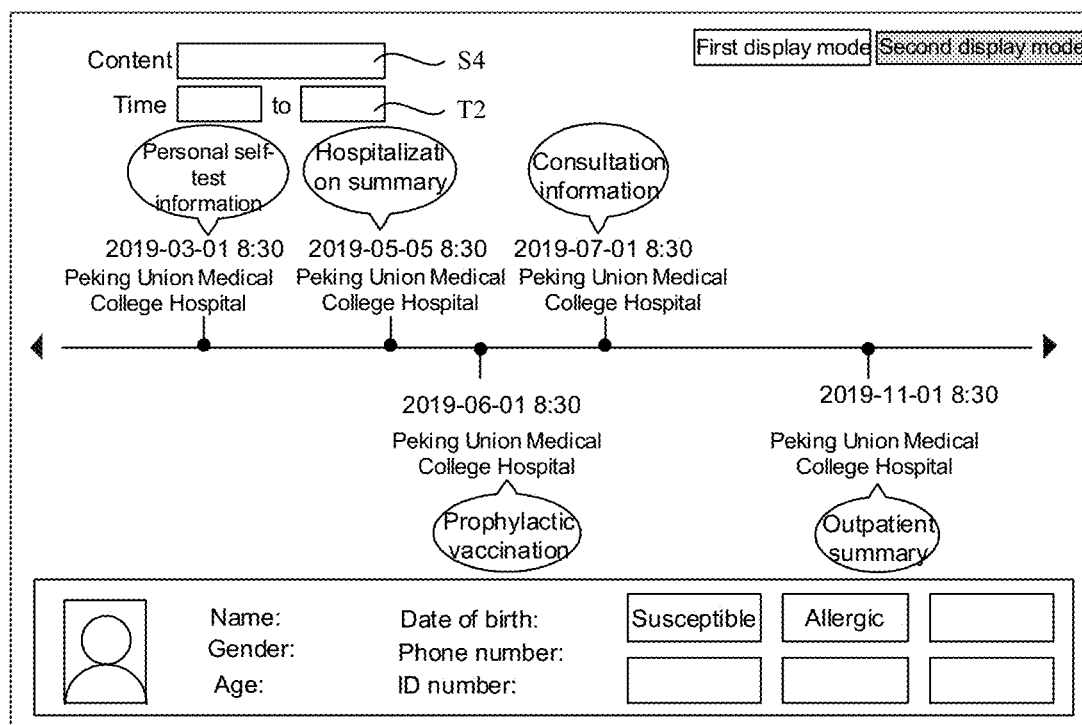
FIG. 8 is a schematic diagram of a second interface displayed in a second display mode, in accordance with some embodiments.

In some examples, the currently set display mode is the second display mode, and the index item(s) on the second interface displayed in the second display mode are second index item(s). The second index item(s) include at least one medical event. For example, each medical event is presented in the form of time and location. For example, one medical event is "2019-03-01 8:30 Peking Union Medical College Hospital". As shown in FIG. 8, in a case where the second index item(s) include a plurality of medical events, the plurality of medical events will be sorted in chronological order in the form of a time axis. On this basis, the user can move the time axis to the left or right as needed, so as to view a "next medical event" or "previous medical event".

It will be noted that, the "next medical event" refers to a medical event that occurs later than the currently presented medical event with the smallest time span therebetween, and the "previous medical event" refers to a medical event that occurs earlier than the currently presented medical event with the smallest time span therebetween. Those skilled in the art can understand that in a case where the reference medical event is different, the "next medical event" is different, and the "previous medical event" is different.

For example, as shown in FIG. 8, the second interface presents the plurality of medical events in the form of a time axis. The electronic device determines the target index item in response to the second operation of the user on the second interface. Here, the second operation may be clicking on one of the plurality of medical events, and the medical event clicked by the user is the target index item. For example, the target index item is a medical event "2019-03-01 8:30 Peking Union Medical College Hospital". Then, the electronic device displays the fifth interface in response to the second operation, the fifth interface presenting the medical information (for example, including symptom, general examination, question of consultation, test, etc.) of the target patient matched with the medical event "2019-03-01 8:30 Peking Union Medical College Hospital".

In some other embodiments, as shown in FIG. 8, the currently set display mode is the second display mode, and the index item(s) on the second interface displayed in the second display mode further include first index item(s) corresponding to respective second index item(s). That is, the index items on the second interface include the second index item(s) and the first index item(s) corresponding to respective second index item(s).

The first index item serves as an identification, and it may be in the form of a piece of text, an icon, a symbol, etc., which is not limited in the present disclosure.

On this basis, S40 includes S421' to S424'.

In S421', the target index item is determined, and the first index item corresponding to the target index item is determined in response to the second operation of the user on the second interface. The target index item is one of the second index item(s).

Here, the second operation of the user on the second interface may be clicking on the first index item corresponding to the target index item.

For example, as shown in FIG. 8, the second index items include a plurality of medical events, for example, a first medical event "2019-03-01 8:30 Peking Union Medical College Hospital", a second medical event "2019-05-05 8:30 Peking Union Medical College Hospital", a third medical event "2019-06-01 8:30 Peking Union Medical College Hospital", a fourth medical event "2019-07-01 8:30 Peking Union Medical College Hospital", and a fifth medical event "2019-11-01 8:30 Peking Union Medical College Hospital". On this basis, the index items on the second interface further include personal self-test information corresponding to the first medical event, hospitalization summary corresponding to the second medical event, prophylactic vaccination corresponding to the third medical event, consultation information corresponding to the fourth medical event, and outpatient summary corresponding to the fifth medical event.

In some examples, as shown in FIG. 8, the second interface displayed in the second display mode further includes a fourth search box S4. The user may input the category of the first index item, such as "hospitalization summary", into the fourth search box S4, and then the electronic device may only present medical event(s) marked with hospitalization summary on the second interface in response to the keyword "hospitalization summary" input by the user into the fourth search box S4.

In some examples, the second interface displayed in the second display mode further includes a plurality of time options. Based on this, the user may filter the medical event(s) through the time option. For example, the plurality of time options are "YYYY-MM-DD to YYYY-MM-DD" (the option indicated by T2 in FIG. 8; "YYYY" indicates the year, "MM" indicates the month, and "DD" indicates the date), "In the last three months", "In the last six months" and "In the last year". If the user selects the time option of "In the last six months", then the second interface displayed in the second display mode only present all medical events related to the target patient within six months before the time of the user's current operation.

In S422', a fifth interface is displayed according to the determined first index item corresponding to the target index item. The fifth interface includes a second detail area and a second list area. The second list area presents at least one medical event of the target patient matched with the first index item corresponding to the target index item.

In S423', a target medical event is determined in response to a fifth operation of the user on the fifth interface. The target medical event is one of the at least one medical event.

In S424', the medical information matched with the target medical event is presented in the second detail area in response to the fifth operation.

In some examples, the fifth interface is the same as the third interface. In such case, the second list area is the same as the first list area, and the second detail area is the same as the first detail area. The fifth operation may be clicking on one of the at least one medical event presented in the second list area.

On the basis of the above, the fifth interface may also present at least one of a fifth search box, a plurality of time options, or a time selector. These features may bring the same beneficial effects as those on the third interface, and details will not be repeated here.

Figure 9:
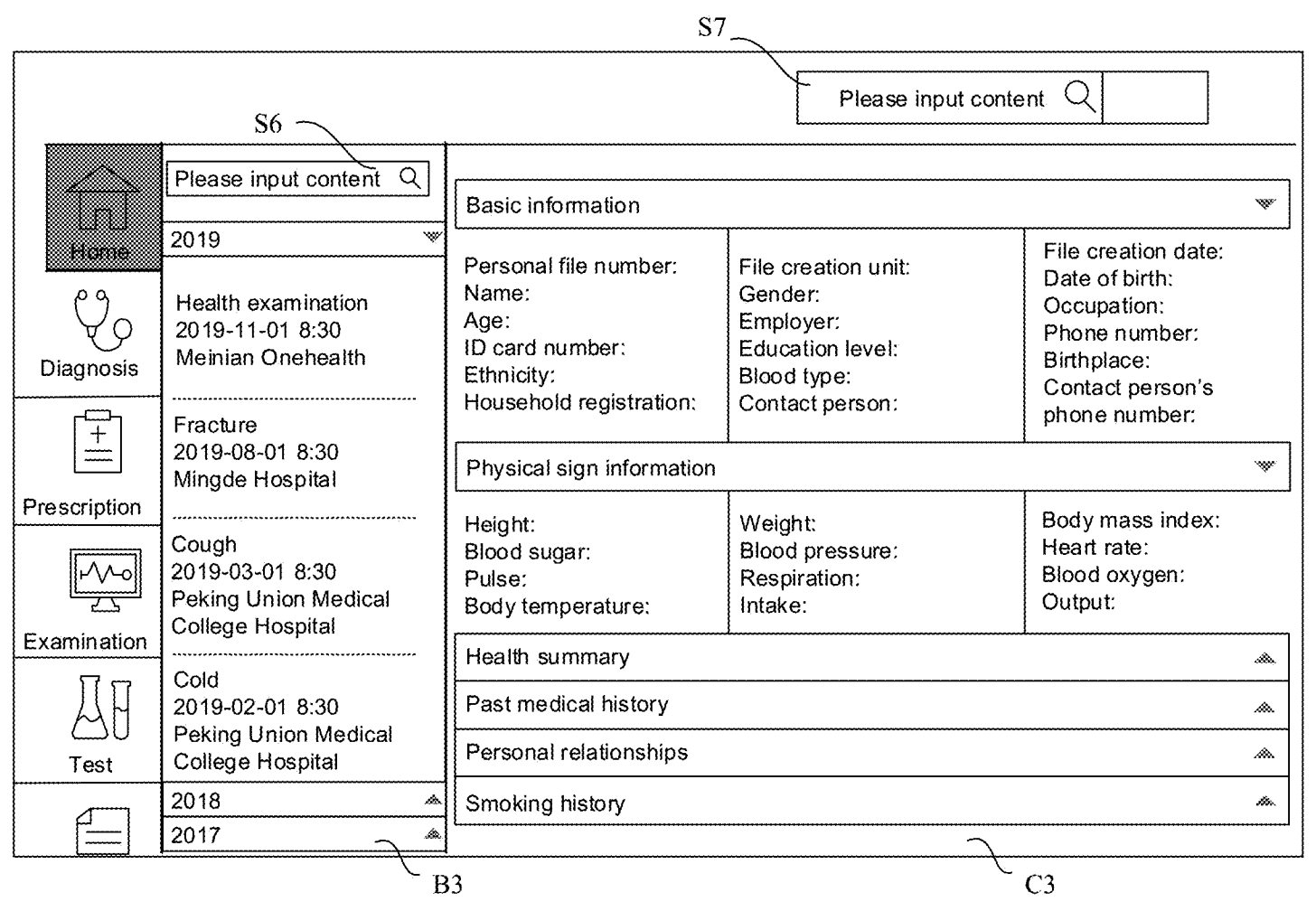

In some embodiments, the at least two display modes further include a third display mode. As shown in FIG. 9, in a case where the currently set display mode is the third display mode, the second interface displayed in the third display mode further includes a third list area (the area indicated by B3 as shown in FIG. 9) and a third detail area (the area indicated by C3 as shown in FIG. 9).

The method of displaying medical information further includes S70.

In S70, the electronic device sets the display mode of the second interface to the third display mode in response to an instruction to switch to the third display mode. The index item(s) on the second interface displayed in the third display mode include third index item(s).

In some examples, the electronic device displays a display mode setting interface in response to an instruction, given by the user on the first interface or the second interface, to set the display mode. As shown in FIG. 4, the display mode setting interface presents a plurality of options corresponding to different display modes, such as the first display mode, the second display mode, and the third display mode. Similar as in S50 and S60, when the user selects the "Third display mode" option on the display mode setting interface, the electronic device switches the display mode of the second interface to the third display mode in response to the instruction to switch to the third display mode.

In some examples, the third index item(s) include at least one of diagnosis, prescription, examination, test, electronic medical record, or charge.

Figure 10:
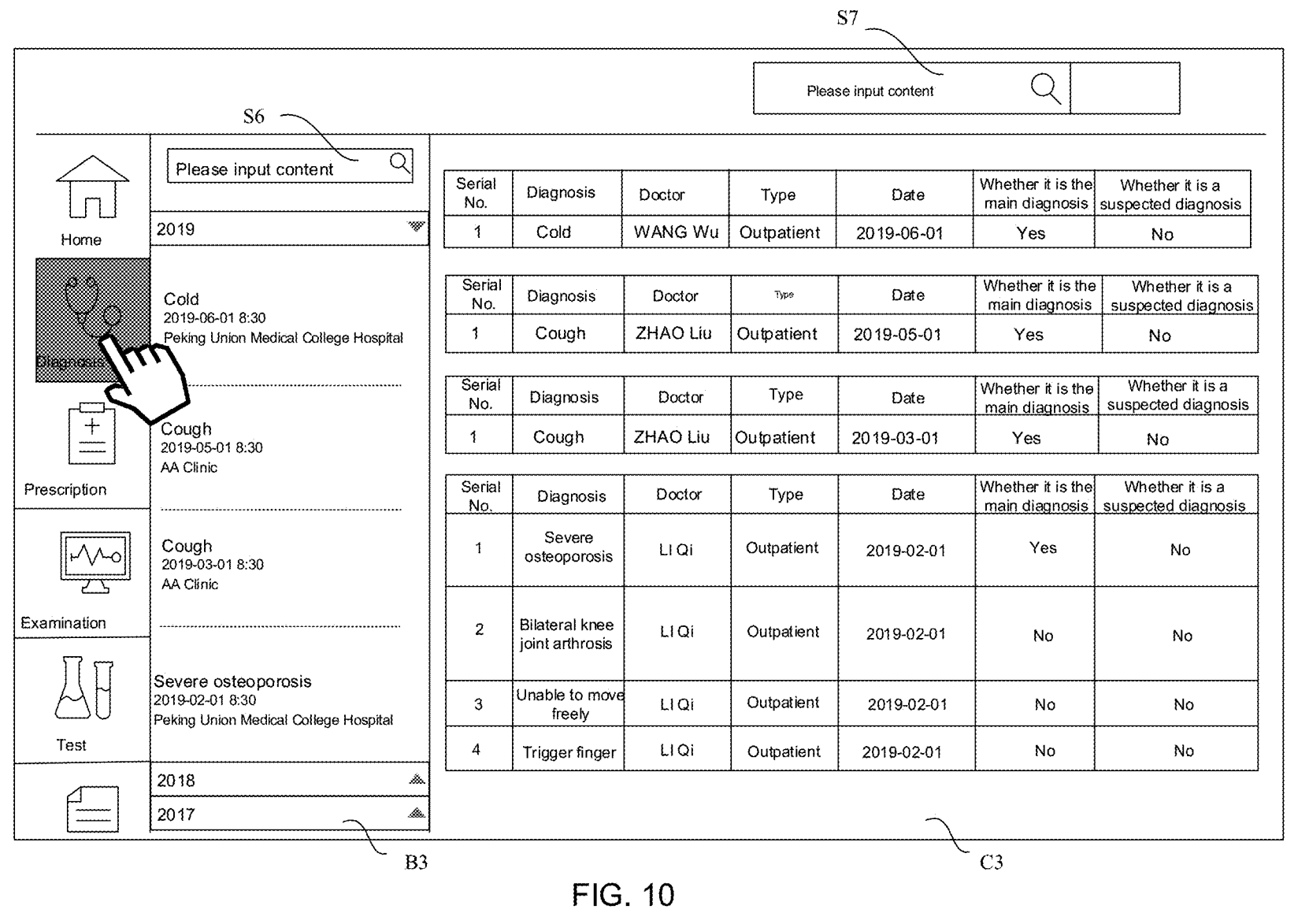

In some examples, as shown in FIGS. 9 and 10, the third index items presented on the second interface include diagnosis, prescription, examination, and test.

It will be noted that, the third index items and the first index items have a main/sub category correspondence, which may be preset by those skilled in the art as needed. Here, the description that the third index items and the first index items have a main/sub category correspondence can be understood as that: the categories of the first index items are main categories, and the categories of the third index items are sub categories. For example, the first index item is "Outpatient summary". According to the Basic Dataset of Health Records for Urban and Rural Residents, medical information related to diagnosis, test or prescription is classified into the category of "Outpatient summary". Then, "Diagnosis", "Test" and "Prescription" are categories of third index items.

In addition, the categories of the third index items included in different categories of the first index items may be the same. For example, one first index item is "Health examination", which includes "Test"; another first index item is "Special disease health management", which also includes "Test".

In some examples, similar to the first index item(s) on the second interface displayed in the first display mode, the user may add or remove a third index item on the second interface displayed in the third display mode as needed, or may sort a plurality of third index items as needed, details of which will not be repeated here.

In some embodiments, the currently set display mode is the third display mode, and the second interface includes a third list area and a third detail area. On this basis, S40 includes S431 and S432.

In S431, the electronic device determines the target index item, and presents at least one medical event matched with the target index item in the third list area in response to the second operation of the user on the second interface. The target index item is one of the third index item(s).

In S432, the electronic device determines a target medical event, and presents the medical information matched with the target medical event in the third detail area in response to a seventh operation of the user on the second interface. The target medical event is one of the at least one medical event matched with the target index item.

For example, the electronic device determines that the target index item is "Diagnosis", and presents at least one medical event of the target patient matched with "Diagnosis" in the third list area in response to the second operation (e.g., clicking on "Diagnosis") of the user on the second interface.

Figure 11:
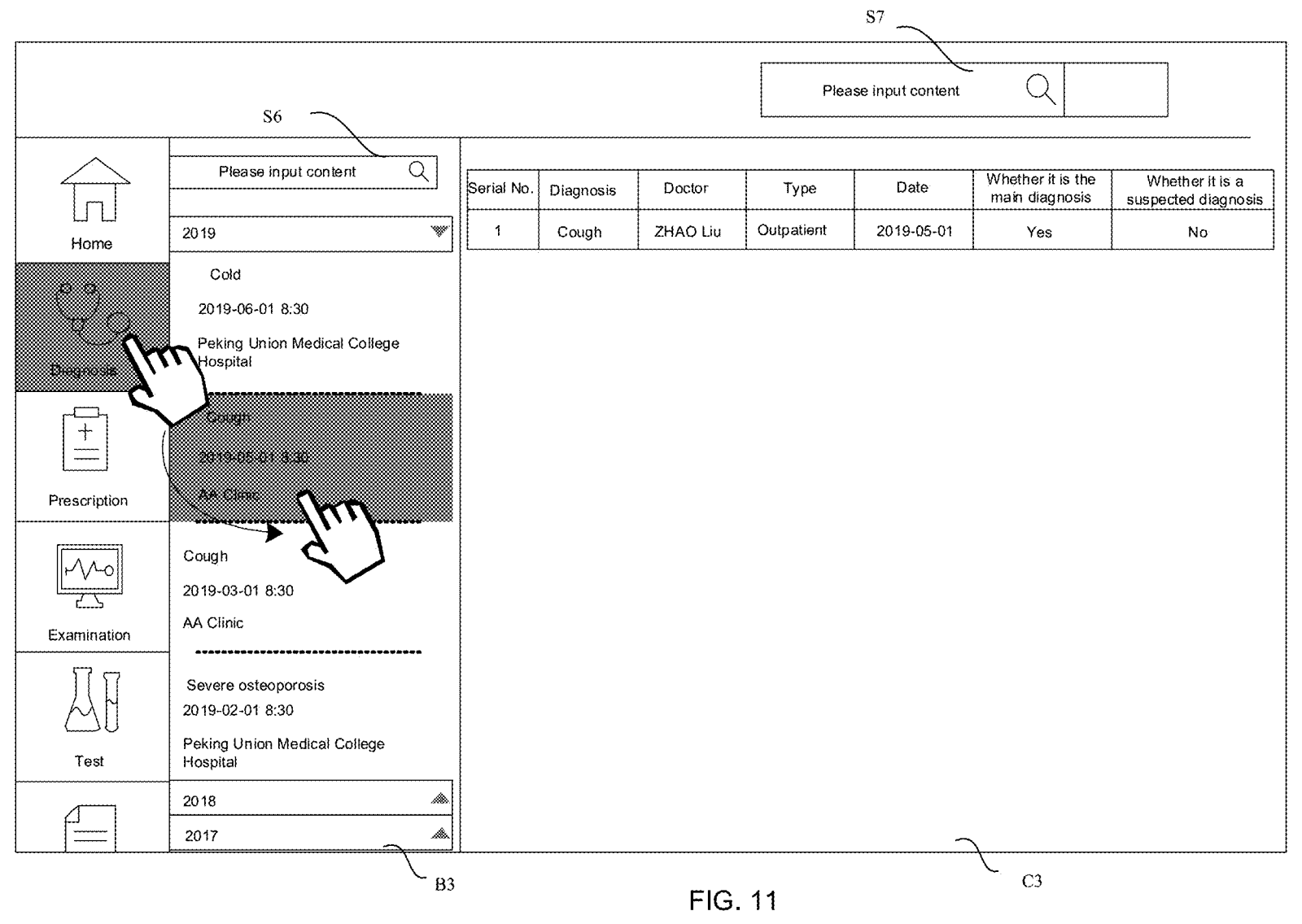

In some examples, the medical event is identified in the form of time, place, and result(s) corresponding to the category of the third index item. For example, as shown in FIGS. 10 and 11, the result(s) corresponding to "Diagnosis" include at least one of "Cold", "Cough", and "Severe osteoporosis", and one medical event is "Cold 2019-06-01 8:30 Peking Union Medical College Hospital".

In some examples, the third list area presents a plurality of medical events of the target patient matched with diagnosis, and the plurality of medical events are sorted in a reverse chronological order. As shown in FIGS. 10 and 11, the third list area includes a plurality of medical events: the medical event listed at the top is "Cold 2019-06-01 8:30 Peking Union Medical College Hospital", the medical event listed at the second place is "Cough 2019-05-01 8:30 AA Clinic", the medical event listed at the third place is "Cough 2019-03-01 8:30 AA Clinic", and the medical event listed at the fourth place is "Severe osteoporosis 2019-02-01 8:30 Peking Union Medical College Hospital".

In addition, the plurality of medical events may also be classified by year, and the user may hide or present the plurality of medical events in the third list area as needed.

The seventh operation of the user on the second interface may be clicking on one of the medical events presented in the third list area. For example, as shown in FIG. 11, the user clicks on the medical event listed at the second place— "Cough 2019-05-01 8:30 AA clinic" in the third list area. Then, the electronic device determines that this medical event is the target medical event, and presents medical information matched with the medical event in the third detail area in response to the seventh operation (clicking on the medical event listed at the second place in the third list area) of the user on the second interface. The medical information includes "Diagnosis: Cough; Doctor: ZHAO Liu, Type: Outpatient; Date: 2019-05-01; Whether it is the main diagnosis: Yes; Whether it is a suspected diagnosis: No".

In some other embodiments, the currently set display mode is the third display mode. As shown in FIG. 10, the second interface includes a third list area and a third detail area. On this basis, S40 includes S431'.

In S431', the electronic device determines the target index item, and presents all medical events matched with the target index item in the third list area, and presents medical information of all medical events matched with the target index item in the third detail area in response to the second operation of the user on the second interface. The target index item is one of the third index item(s).

For example, as shown in FIG. 10, the electronic device determines the target index item and presents the medical information of all medical events matched with the target index item in the third detail area in response to the second operation (e.g., clicking on "Diagnosis").

In yet some other embodiments, the currently set display mode is the third display mode, and the third detail area presents the basic information of the target patient by default.

For example, as shown in FIG. 9, the third detail area presents the basic information of the target patient by default. The basic information includes: personal file number, file creation unit, file creation date, name, gender, date of birth, age, employer, occupation, ID card number, education level, phone number, ethnicity, blood type, birthplace, household registration location, contact person, and contact person's phone number.

In some examples, the third detail area further presents other information matched with the target patient, such as physical sign information, health summary, past medical history, personal relationships, and smoking history, by default.

For example, as shown in FIG. 9, the physical sign information matched with the target patient presented in the third detail area includes: height, weight, body mass index, blood sugar, blood pressure, heart rate, pulse, respiration, blood oxygen, body temperature, intake, and output.

Based on the above description, in some examples, the second interface further presents a category option. For example, the category option is "Home". The electronic device presents the basic information of the target patient and other information as described above in the third detail area in response to the operation of clicking on the category option (e.g., clicking on "Home") by the user on the second interface.

On the basis of the above, as shown in FIGS. 9 to 11, the third list area may further include a sixth search box S6, which has the same beneficial effects as the third search box S3 on the third interface and the fifth search box on the fifth interface, and details will not be repeated here.

In addition, as shown in FIGS. 9 to 11, the second interface displayed in the third display mode may further include a seventh search box S7. The user may input a keyword related to the content presented in the third list area or the third detail area into the seventh search box S7, so as to facilitate searching as needed.

In addition, the second interface displayed in the third display mode may further include a time selector or a plurality of time options, which have the same beneficial effects as the third interface and the fifth interface, and details will not be repeated here.

In some embodiments, the medical information presented in the first detail area, the second detail area, and the third detail area all include at least one item name and medical data corresponding to each item name.

The current display mode is the first display mode, and the method of displaying medical information further includes S41.

In S41, a target item name is determined, and a fourth interface is displayed in response to a fourth operation of the user on the third interface. The target item name is one of the at least one item name. The fourth interface presents medical data of the target patient matched with the target item name in at least two medical events.

The current display mode is the second display mode, and the method of displaying medical information further includes S42.

In S42, a target item name is determined, and a fourth interface is displayed in response to a sixth operation of the user on the fifth interface. The target item name is one of the at least one item name. The fourth interface presents medical data of the target patient matched with the target item name in at least two medical events.

The current display mode is the third display mode, and the method of displaying medical information further includes S43.

In S43, a target item name is determined, and a fourth interface is displayed in response to an eighth operation of the user on the second interface. The target item name is one of the at least one item name. The fourth interface presents medical data of the target patient matched with the target item name in at least two medical events.

It will be noted that, the medical data matched with the target item name may be presented on the fourth interface in the form of a list, a two-dimensional graph, a three-dimensional graph, etc., which is not limited in the present disclosure.

In addition, there may be one or more medical events matched with the target item name. The embodiments of the present disclosure are illustrated by taking examples in which there are at least two medical events matched with the target item name. It can be understood that, in a case where there is only one medical event of the target patient matched with the target item name, the fourth interface will not present any content.

In some examples, the fourth interface may further present medical data presenting form options, and different medical data presenting form options correspond to different medical data presenting forms.

On this basis, the method of displaying medical information further includes: presenting, by the electronic device, the medical data matched with the target item name in different medical data presenting forms on the fourth interface in response to an instruction to switch a medical data presenting form. For example, if the instruction to switch a medical data presenting form is an instruction to switch to a list form, the electronic device will present the medical data matched with the target item name in the form of a list on the fourth interface in response to the instruction to switch to the list form. Therefore, the user may switch the medical data presenting form as needed, so as to learn more about the patient and provide strong support for the treatment of the patient.

Figure 12A:
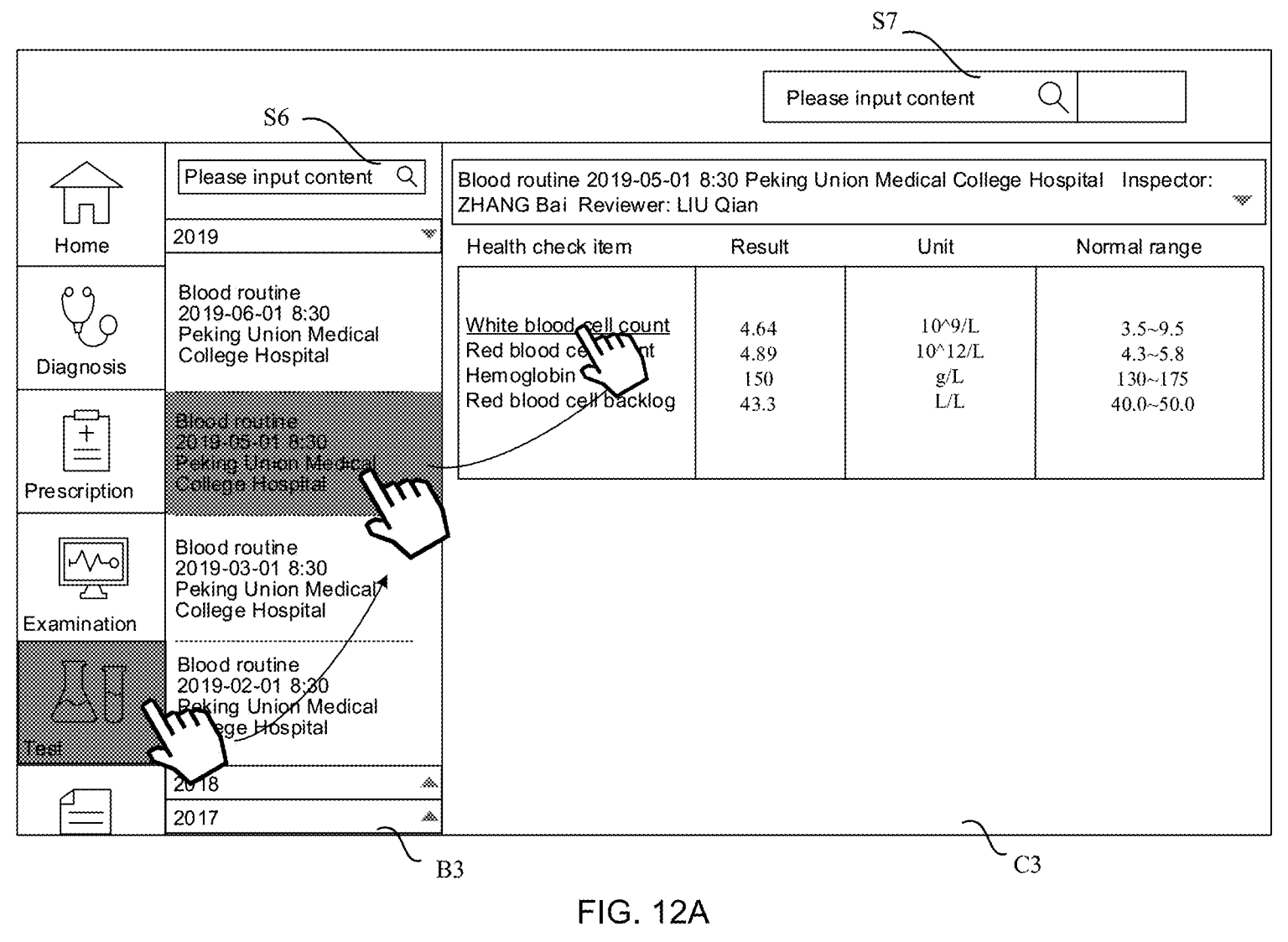
Figure 12B:
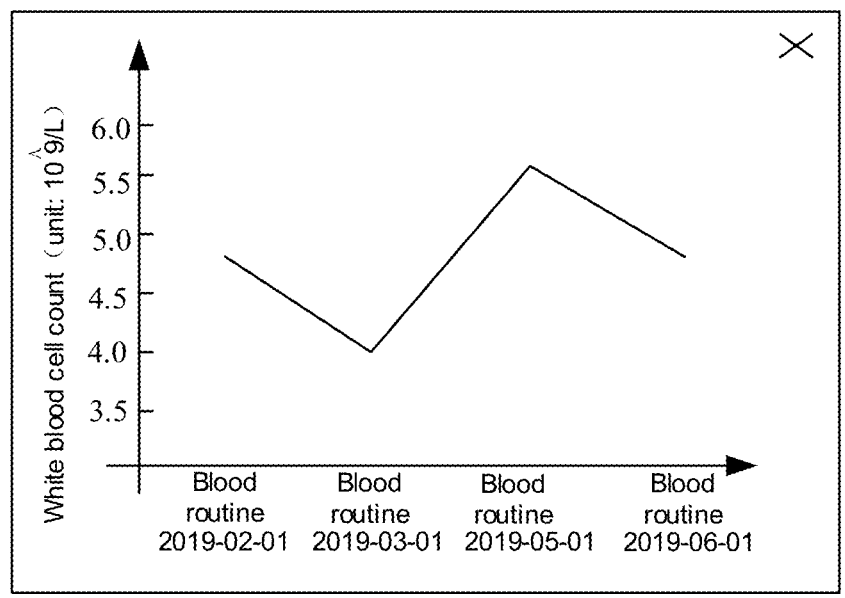
FIG. 12B is a schematic diagram of a fourth interface, in accordance with some embodiments.

For example, as shown in FIGS. 12A and 12B, if the target patient is "WANG Xiaoming" and the target medical event is "Blood routine 2019-05-01 Peking Union Medical College Hospital", then the third detail area C3 on the second interface displayed in the third display mode will present a plurality of item names matched with the target medical event and corresponding medical data. For example, one of the item names is "White blood cell count", and the corresponding value is 4.64. The electronic device determines that white blood cell count is the target item name, and displays the fourth interface in response to the eighth operation (e.g., clicking on "White blood cell count") of the user on the second interface.

If four medical events of the target patient "WANG Xiaoming" all have the item name "White blood cell count", then the fourth interface will present medical data in the four medical events of "WANG Xiaoming" that is matched with the item name "White blood cell count". For example, the fourth interface presents how the white blood cell count changes in the four medical events in the form of a trend graph with time as the abscissa and white blood cell count as the ordinate, thereby making it more convenient for the user to learn about the patient comprehensively and providing strong support for the treatment of the patient.

It will be noted that, the fourth operation and the sixth operation are similar to the eighth operation in the foregoing example, and the beneficial effects produced in S41 and S42 are the same as the beneficial effects produced in S43. Details will not be repeated here.

In some embodiments, the method of displaying medical information further includes S01.

In S01, medical information of a plurality of patients is obtained from servers of a plurality of medical institutions and is stored in a database.

In the embodiments of the present disclosure, the target patient is one of the plurality of patients.

On this basis, the step of determining the target index item, and displaying the medical information of the target patient matched with the target index item in response to the second operation (S40), includes S40A and S40B.

In S40A, the target index item is determined, and the medical information of the target patient matched with the target index item is obtained from the database in response to the second operation.

In S40B, the medical information of the target patient matched with the target index item is displayed.

Figure 13:
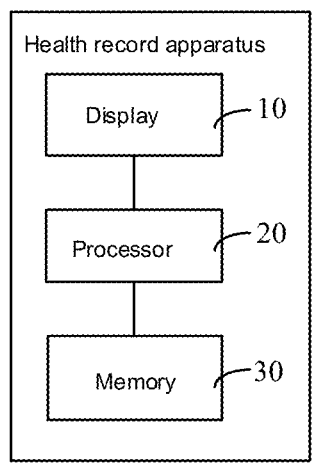
FIG. 13 is a structural diagram of a health record apparatus, in accordance with some embodiments.

Some embodiments of the present disclosure provide a health record apparatus. As shown in FIG. 13, the health record apparatus includes a display 10 and a processor 20, and the display 10 is coupled to the processor 20.

The display 10 is configured to display images.

The processor 20 is configured to: control the display 10 to display a first interface; determine a target patient in response to at least a first operation of the user on the first interface; and control the display 10 to display a second interface in a currently set display mode according to the determined target patient. The second interface presents at least index item(s) of medical information of the target patient. The currently set display mode is one of at least two display modes including a first display mode and a second display mode, and the index item(s) on the second interface corresponding to different display modes are different.

The processor 20 is further configured to: determine a target index item in response to a second operation of the user on the second interface; and control the display 10 to display medical information of the target patient matched with the target index item according to the determined target index item. The target index item is one of the index item(s).

In some embodiments, the processor is further configured to: set the display mode of the second interface to the first display mode in response to an instruction to switch to the first display mode; and set the display mode of the second interface to the second display mode in response to an instruction to switch to the second display mode. The index item(s) on the second interface displayed in the first display mode include first index item(s). The index item(s) on the second interface displayed in the second display mode include second index item(s).

In some other embodiments, the at least two display modes further include a third display mode. On this basis, the processor is further configured to set the display mode of the second interface to the third display mode in response to an instruction to switch to the third display mode. The index item(s) on the second interface displayed in the third display mode include third index item(s).

In some embodiments, the processor is further configured to obtain medical information of a plurality of patients from servers of a plurality of medical institutions. Herein, the medical institution includes at least one of a clinic, an infirmary, a hospital, a physical examination institution, and a health service station.

On this basis, as shown in FIG. 13, the health record apparatus further includes a memory 30. The memory 30 is coupled to the processor 20. The memory 30 is configured to store the medical information of the plurality of patients obtained by the processor in a database.

The processor is further configured to obtain the medical information of the target patient matched with the target index item from the database according to the determined target index item, and control the display 10 to display the medical information.

In some examples, the processor obtains the medical information of the plurality of patients from the servers of the plurality of cooperating medical institutions through an application programming interface (API). For example, based on the Basic Dataset of Health Records for Urban and Rural Residents, the processor classifies and stores the medical information in the database.

The health record apparatus provided in the embodiments of the present disclosure has the same beneficial effects as the method of displaying medical information described above, and details will not be repeated here.

It will be noted that the health record apparatus may be the main body of implementation of the method of displaying medical information provided in any one of the above embodiments, i.e., the electronic device.

Some embodiments of the present disclosure provide a computer device. The computer device includes a memory and a processor. The memory has stored thereon computer program instructions that are executable on the processor. The method of displaying the medical information as described above is implemented when the processor executes the computer program instructions. The computer device may be the health record apparatus described above.

Some embodiments of the present disclosure provide a computer-readable storage medium (e.g., a non-transitory computer-readable storage medium). The computer-readable storage medium has stored thereon computer program instructions. When the computer program instructions run on a processor, the processor executes one or more steps in the method of displaying medical information as provided in any one of the above embodiments.

For example, the computer-readable storage medium may include, but is not limited to, a magnetic storage device (e.g., a hard disk, a floppy disk or magnetic tape), an optical disk (e.g., a compact disk (CD), a digital versatile disk (DVD), etc.), a smart card or a flash memory device (e.g., an erasable programmable read-only memory (EPROM), a card, a stick or a key driver). The various kinds of computer-readable storage media described in the present disclosure may represent one or more devices and/or other machine-readable storage media for storing information. The term "machine-readable storage media" may include, but is not limited to, wireless channels and various kinds of other media capable of storing, containing and/or carrying instructions and/or data.

The above descriptions are merely some specific implementation manners of the present disclosure, but the protection scope of the present disclosure is not limited thereto. Any person skilled in the art could conceive of changes or replacements within the technical scope disclosed in the present disclosure, which shall all be included in the protection scope of the present disclosure. Therefore, the protection scope of the present disclosure shall be subject to the protection scope of the claims.

What is claimed is:

1. A method of displaying medical information, comprising:
    displaying a first interface, the first interface being a search interface, the search interface including a first search box and a display area located below the first search box, wherein the display area is used to display search history records;
    determining a target patient in response to at least a first operation of a user on the first interface, wherein the first operation includes inputting a keyword into the first search box on the search interface;
    displaying a second interface in a currently set display mode, the second interface presenting at least one index item of medical information of the target patient, the currently set display mode being one of at least two display modes including a first display mode and a second display mode, the at least two display modes further including a third display mode, and the at least one index item on the second interface corresponding to different display modes being different; and
    determining a target index item, the target index item being one of the at least one index item, and displaying medical information of the target patient matched with the target index item in response to a second operation of the user on the second interface; and
    the method further comprising:
    setting the display mode of the second interface to the first display mode in response to an instruction to switch to the first display mode, the at least one index item on the second interface displayed in the first display mode including at least one first index item;
    setting the display mode of the second interface to the second display mode in response to an instruction to switch to the second display mode, the at least one index item on the second interface displayed in the second display mode including at least one second index item; and
    setting the display mode of the second interface to the third display mode in response to an instruction to switch to the third display mode, the at least one index item on the second interface displayed in the third display mode including at least one third index item, wherein
    the at least one first index item includes a plurality of first index items, the at least one third index item includes a plurality of third index items, the plurality of third index items and the plurality of first index items have a main/sub category correspondence, categories of the plurality of first index items are main categories, categories of the plurality of third index items are sub categories, and the categories of the plurality of third index items included in different categories of the plurality of first index items are the same.

2. The method of displaying medical information according to claim 1, wherein the at least one first index item include at least one of personal self-test information, health examination, outpatient summary, maternal and child health, prophylactic vaccination, public health incident report, special disease health management, hospitalization summary, consultation information, referral or transfer information; or
    the at least one second index item include at least one medical event.

3. The method of displaying medical information according to claim 1, wherein the currently set display mode is the first display mode;
    determining the target index item, and displaying the medical information of the target patient matched with the target index item in response to the second operation, includes:
    determining the target index item in response to the second operation;
    displaying a third interface according to the determined target index item, the third interface including a first list area and a first detail area, and the first list area presenting at least one medical event of the target patient matched with the target index item; and
    determining a target medical event, the target medical event being one of the at least one medical event, and presenting the medical information matched with the target medical event in the first detail area in response to a third operation of the user on the third interface.

4. The method of displaying medical information according to claim 3, wherein the medical information includes at least one item name and medical data corresponding to each item name; the at least one medical event includes at least two medical events; and the method further comprises:
determining a target item name, the target item name being one of the at least one item name, and displaying a fourth interface, the fourth interface presenting medical data of the target patient matched with the target item name in the at least two medical events, in response to a fourth operation of the user on the third interface.

5. The method of displaying medical information according to claim 1, wherein the currently set display mode is the second display mode, and determining the target index item, and displaying the medical information of the target patient matched with the target index item in response to the second operation, includes:

determining the target index item in response to the second operation; and
displaying a fifth interface according to the determined target index item, the fifth interface presenting the medical information of the target patient matched with the target index item.

6. The method of displaying medical information according to claim 5, wherein the medical information includes at least one item name and medical data corresponding to each item name; the at least one medical event includes at least two medical events; and the method further comprises:
determining a target item name, the target item name being one of the at least one item name, and displaying a fourth interface, the fourth interface presenting medical data of the target patient matched with the target item name in the at least two medical events, in response to a sixth operation of the user on the fifth interface.

7. The method of displaying medical information according to claim 1, wherein the currently set display mode is the second display mode, and the at least one index item further include a first index item corresponding to each second index item;

determining the target index item, and displaying the medical information of the target patient matched with the target index item in response to the second operation, includes:
determining the target index item, the target index item being one of the at least one second index item, and determining a first index item corresponding to the target index item in response to the second operation;
displaying a fifth interface according to the determined first index item corresponding to the target index item, the fifth interface including a second detail area and a second list area, and the second list area presenting at least one medical event of the target patient matched with the first index item corresponding to the target index item;
determining a target medical event in response to a fifth operation of the user on the fifth interface, the target medical event being one of the at least one medical event; and presenting the medical information matched with the target medical event in the second detail area in response to the fifth operation.

8. The method of displaying medical information according to claim 7, wherein the medical information includes at least one item name and medical data corresponding to each item name; the at least one medical event includes at least two medical events; and the method further comprises:
determining a target item name, the target item name being one of the at least one item name, and displaying a fourth interface, the fourth interface presenting medical data of the target patient matched with the target item name in the at least two medical events, in response to a sixth operation of the user on the fifth interface.

9. The method of displaying medical information according to claim 1, wherein the at least one third index item include at least one of diagnosis, prescription, examination, test, electronic medical record, or charge.

10. The method of displaying medical information according to claim 1, wherein the currently set display mode is the third display mode, and the second interface includes at least a third list area and a third detail area;

determining the target index item, and displaying the medical information of the target patient matched with the target index item in response to the second operation, includes:
determining the target index item, the target index item being one of the at least one third index item, and presenting at least one medical event matched with the target index item in the third list area in response to the second operation; and
determining a target medical event, the target medical event being one of the at least one medical event, and presenting the medical information matched with the target medical event in the third detail area in response to a seventh operation of the user on the second interface.

11. The method of displaying medical information according to claim 10, wherein the medical information includes at least one item name and medical data corresponding to each item name; the at least one medical event includes at least two medical events; and the method further comprises:
determining a target item name, the target item name being one of the at least one item name, and displaying a fourth interface, the fourth interface presenting medical data of the target patient matched with the target item name in the at least two medical events, in response to an eighth operation of the user on the second interface.

12. The method of displaying medical information according to claim 1, further comprising:
obtaining medical information of a plurality of patients from servers of a plurality of medical institutions, and storing the medical information in a database, wherein
determining the target index item, and displaying the medical information of the target patient matched with the target index item in response to the second operation, includes:
determining the target index item, obtaining the medical information of the target patient matched with the target index item from the database, and displaying the medical information in response to the second operation.

13. A computer device, comprising a memory and a processor, wherein the memory has stored thereon computer program instructions that are executable on the processor; and the method of displaying medical information according to claim 1 is implemented when the processor executes the computer program instructions.

14. A non-transitory computer-readable storage medium having stored thereon computer program instructions, wherein when the computer program instructions run on a processor, the processor executes one or more steps in the method of displaying medical information according to claim 1.

15. A health record apparatus, comprising:
a display configured to display images; and
a processor coupled to the display and configured to: control the display to display a first interface, the first interface being a search interface, the search interface including a first search box and a display area located below the first search box, wherein the display area is used to display search history records; determine a target patient in response to at least a first operation of the user on the first interface, wherein the first operation includes inputting a keyword into the first search box on the search interface; control the display to display a second interface in a currently set display mode according to the determined target patient, the second interface presenting at least one index item of medical information of the target patient, the currently set display mode being one of at least two display modes including a first display mode and a second display mode, the at least two display modes further including a third display mode, and the at least one index item on the second interface corresponding to different display modes being different; determine a target index item in response to a second operation of the user on the second interface, the target index item being one of the at least one index item; and control the display to display medical information of the target patient matched with the target index item according to the determined target index item; and the processor being further configured to:

set the display mode of the second interface to the first display mode in response to an instruction to switch to the first display mode, the at least one index item on the second interface displayed in the first display mode including at least one first index item;
set the display mode of the second interface to the second display mode in response to an instruction to switch to the second display mode, the at least one index item on the second interface displayed in the second display mode including at least one second index item; and
set the display mode of the second interface to the third display mode in response to an instruction to switch to the third display mode, the at least one index item on the second interface displayed in the third display mode including at least one third index item, wherein
the at least one first index item includes a plurality of first index items, the at least one third index item includes a plurality of third index items, the plurality of third index items and the plurality of first index items have a main/sub category correspondence, categories of the plurality of first index items are main categories, categories of the plurality of third index items are sub categories, and the categories of the plurality of third index items included in different categories of plurality of the first index items are the same.

16. The health record apparatus according to claim 15, wherein the processor is further configured to obtain medical information of a plurality of patients from servers of a plurality of medical institutions; and
the health record apparatus further comprises:
a memory coupled to the processor and configured to store the medical information of the plurality of patients obtained by the processor in a database, wherein
the processor is further configured to obtain the medical information of the target patient matched with the target index item from the database according to the determined target index item, so as to control the display to display the medical information.

* * * * *